United States Patent [19]
Turp et al.

[11] 3,994,287
[45] Nov. 30, 1976

[54] TROCAR

[75] Inventors: Gerald Turp, Neuchatel; Mohammad Ahmad, Ville Lemoyne, both of Canada

[73] Assignee: Centre de Recherche Industrielle du Quebec, Canada

[22] Filed: July 1, 1974

[21] Appl. No.: 484,927

[52] U.S. Cl. .............................. 128/6; 128/214.4; 128/347; 277/188 R
[51] Int. Cl.² .................... A61B 1/06; A61B 17/34; A61M 5/32
[58] Field of Search .................. 128/6, 214.4, 347; 277/188 R

[56] References Cited
UNITED STATES PATENTS

| | | | |
|---|---|---|---|
| 737,293 | 8/1903 | Summerfeldt | 128/347 X |
| 2,438,457 | 3/1948 | Schlosser | 277/188 R X |
| 2,743,119 | 4/1956 | Covert et al. | 277/188 R X |
| 2,746,450 | 5/1956 | Lady et al. | 128/6 |
| 2,766,082 | 10/1956 | Ritchey | 277/188 R X |
| 3,127,894 | 4/1964 | Smith | 128/347 |
| 3,313,299 | 4/1967 | Spademan | 128/347 X |
| 3,459,189 | 8/1969 | Alley et al. | 128/347 |
| 3,585,996 | 6/1971 | Reynolds et al. | 128/214.4 |
| 3,653,388 | 4/1972 | Tenckhoff | 128/347 |
| 3,717,151 | 2/1973 | Collett | 128/347 |
| 3,724,922 | 4/1973 | Jones | 128/6 X |
| 3,760,797 | 9/1973 | Stauffer | 128/6 |
| 3,763,860 | 10/1973 | Clarke | 128/347 X |

*Primary Examiner*—Channing L. Pace
*Attorney, Agent, or Firm*—Cushman, Darby & Cushman

[57] ABSTRACT

The disclosure herein describes a trocar particularly intended for use in laparoscopic tubal cauterization and formed of: a puncturing sharp-pointed instrument, a cannula with a flange at one end thereof, a flexible insulating ring which is received in the flange recess bore, and a collar secured in the flange bore. The collar retains the ring in the flange while allowing it to flex as the puncturing instrument is introduced in the cannula or disassociated therefrom. The puncturing instrument, cannula and collar are made of inexpensive bio-compatible plastic materials while the ring is made of rubber; consequently, the trocar is disposable after use.

10 Claims, 5 Drawing Figures

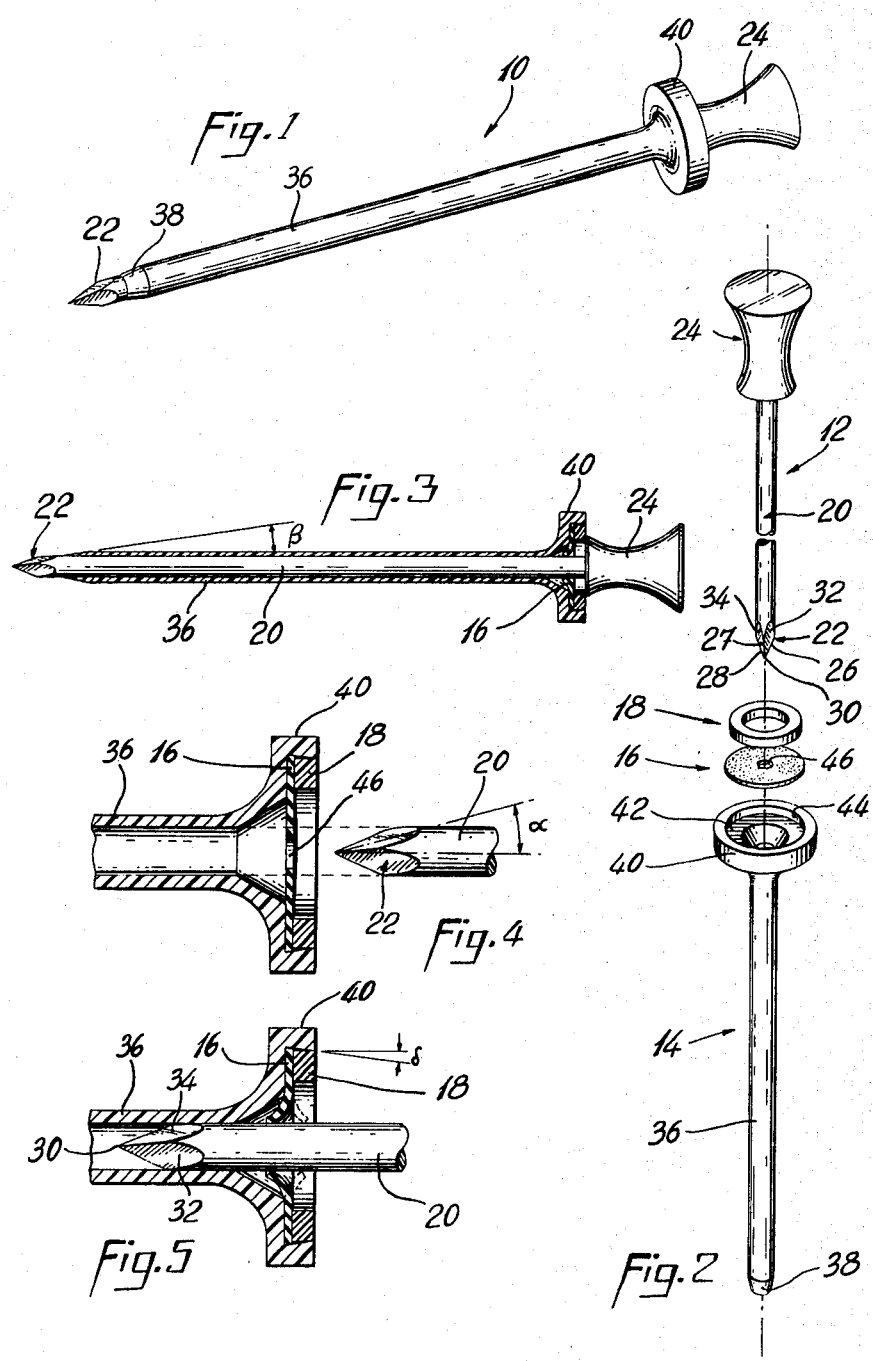

TROCAR

FIELD OF THE INVENTION

The present invention relates to a surgical instrument for piercing a body cavity and for thereafter providing a means for communicating inside the cavity, e.g., to drain or deliver fluids or to perform other surgical acts.

BACKGROUND OF THE INVENTION

One situation which requires the use of trocars, is laparoscopic tubal cauterization where $CO_2$ is insufflated into the abdominal cavity of a patient under anesthesia. The trocar, consisting principally of a sharp-pointed puncturing instrument fitted with a cannula, pierces the body cavity whereafter the puncturing element is withdrawn leaving the hollow cannula in place to receive a laparoscope for examination of the abdominal cavity. Further explanation of the cauterization procedure as well as of a novel instrument therefor may be found in Canadian patent application Ser. No. 175,625 filed July 4, 1973 in the name of Jacques Rioux et al.

Present trocars used in this type of surgical act are made of metal and, consequently, must be cleaned and sterilized after each use. Hence, there is need for a disposable trocar which is simple and inexpensive and which will perform just as efficiently as the present metallic trocar.

Some disposable trocars exist; however, none are constructed so that they may be used for laparoscopic tubal cauterization. Most are designed primarily for allowing the passage of fluids to and from the body cavity. For use with laparoscopic tubal cauterization, the trocar must be structured to prevent any leak of $CO_2$ which is under pressure (about 5 p.s.i.) inside the abdominal cavity. It is essential that the abdomen remain insufflated during the entire procedure to allow the surgeon to clearly see and to freely work inside the cavity.

OBJECTS

It is a principal object of this invention to provide a new improvement in the construction of a surgical apparatus for piercing a body cavity and for thereafter providing a communication with the cavity.

It is also an object of this invention to provide a simple, inexpensive and, consequently disposable, trocar for use in laparoscopic tubal cauterization.

It is still another object of the present invention to provide a trocar with a hollow cannula which is in leakproof engagement with the puncturing instrument or with the instrument which is subsequently associated.

It is a further object of this invention to provide a trocar with a sharp-pointed puncturing element which pierces the cavity wall without damaging the same thereby ensuring that the lesion done will easily heal thereafter without leaving an ugly scar.

SUMMARY OF THE INVENTION 1

These objects are accomplished according to the present invention by the provision of a trocar which comprises, in combination: a sharp-pointed puncturing instrument made of a bio-compatible plastic material; a cannula also made of a bio-compatible plastic material and having a flange at one end thereof; a flexible insulating member secured in the cannula flange and in constricting engagement with the puncturing instrument; and a collar tightly fitted in the cannula flange and securing the flexible member in place allowing, however, a portion of the member to flex in the longitudinal axis of the cannula as the puncturing instrument is introduced in the cannula or disassociated therefrom.

Advantageously, the flexible insulating member which constrictively surrounds the puncturing element is made of a resilient material which will allow it to remain in tight frictional engagement with the shank of the puncturing element as the latter is inserted in the cannula or disassociated therefrom. This engagement will prevent any leak of the gas under pressure inside the abdominal cavity. Further, the collar must be sufficiently tight in the flange of the cannula to prevent pressure leaks between its outer edge and the cannula flange.

Other objects and further characteristic features of the present invention will become apparent from the detailed description given hereinafter; it should be understood however, that the detailed description, while indicating preferred embodiments of the invention, is given by way of illustration only, since various changes and modifications within the spirit and scope of the invention will become apparent to those skilled in the art from this detailed description.

BRIEF DESCRIPTION OF THE DRAWINGS

FIG. 1 is a perspective view of a preferred embodiment of a trocar in accordance with the present invention;

FIG. 2 is an exploded view thereof;

FIG. 3 is a longitudinal view showing the puncturing instrument inside the hollow cannula; and FIGS. 4 and 5 are enlarged views illustrating the insulating member before and after the puncturing instrument is introduced in the cannula.

DESCRIPTION OF A PREFERRED EMBODIMENT

Referring more particularly to the drawing wherein like numerals indicate like or corresponding parts throughout the several views, a preferred embodiment of a trocar 10 in accordance with the invention comprises the following major components: a puncturing element 12, a cannula 14, a flexible ring 16 and a collar 18.

The trocar hereinbelow described is particularly intended for use during laparoscopic tubal cauterization. In this type of surgical intervention, the abdominal cavity of a patient is first insufflated with $CO_2$. A trocar is then used to pierce the cavity wall. The puncturing element of the trocar is subsequently disassociated with the cannula, a portion of which is retained inside the cavity. A laparoscope is immediately introduced through the cannula to allow the surgeon to see inside the abdominal cavity. Another incision is made in the abdominal wall and a cauterization instrument is introduced therein for surgery. It is therefore essential that, during the entire operation, the abdominal cavity remains insufflated with $CO_2$ under pressure, about 5 p.s.i. The present invention is therefore concerned to provide a simple, inexpensive and, consequently disposable, trocar which is designed to maintain the requirements of such procedure.

The puncturing instrument 12 of the trocar 10 includes an elongated shank portion 20 terminating at one extremity thereof with a sharp pointed end 22 and at the other extremity thereof with a finger knob 24.

End 22 has a pyramidal shape defining three spaced cutting edges 26, 27, 28 diverging from a tip 30 and defining three smooth surfaces, two of which are shown at 32 and 34. These surfaces make an angle $\alpha$ (see FIG. 4) with the longitudinal axis of the shank 20; one preferred angle is 15°.

The puncturing element 12 is entirely made of a bio-compatible plastic material, the characteristics of which being that it is capable of being molded into one piece, that the straight narrow shank portion 20 be rigid with, however, a certain degree of flexibility to prevent it from being easily broken during the piercing procedure, that it be sterilizable, for example, by gamma rays, that it be non-filiform to thereby provide a smoothness on the cutting surfaces 32, 34 which will allow the instrument to perforate without excessive friction on the membrane and without leaving filaments on the perforated membrane. Various materials are available which are adapted to serve these requirements; among these, are certain polycarbonates or acrylics. Transparent Lexan (trademark) is particularly well suited for this purpose. The reason for using a puncturing element made of a transparent material is to indicate to the surgeon when the light-emitting laparoscope is inside the abdomen and as he pierces again the abdomen wall (usually adjacent the pubis area), that the light seen in the finger knob 24 and transmitted via the shank portion 20 is indicative that the trocar has now reached the abdomen cavity.

The cannula 14 of the trocar 10 includes a hollow elongated portion 36 which is adapted to come in surrounding engagement with the shank portion 20 of the puncturing element 12. End 38 of portion 36 is tapered and forms an angle $\beta$ (see FIG. 3) with respect to the longitudinal axis of the hollow portion 36 of the cannula. One preferred angle is 10°. The pointed-end 22 of the puncturing element extends, when received through cannula 14, adjacent the tapered end 38 so that the latter will give a certain continuity as the trocar pierces the cavity wall. The opposite end of cannula 14 includes a flange portion 40 equipped with a circular recess 42, the side walls 44 of which are slightly inclined of an angle $\delta$ (see FIG. 5) with respect to the longitudinal axis of the cannula; one preferred angle is 5°.

The cannula 14 is made of a bio-compatible plastic material, the characteristics of which being that it be sufficiently rigid for the thin walls it has, that it be sterilizable (gamma rays), that it be capable of being molded in one piece and that it be non-filiform so as to not leave filaments. Various plastic materials are available which are adapted to serve these requirements; among these, are certain polyamide, acetal, polyethylene and stabilizer-added polyvinylchloride. Materials known under the trademarks nylon, Delrin and Celcon are particularly well suited for this purpose.

In one preferred form, the outer surface of the cannula, at least in its elongated portion 36, has a certain degree of roughness to add to the frictional contact between the cannula and the cavity wall.

The collar 18 is also made of a bio-compatible plastic material. The collar is press-fitted into the recess 42 of the cannula and is retained therein by the inclined sidewalls 44. The engagement of the collar in the recess is seal-tight to prevent leaks of the $CO_2$ under pressure inside the abdominal cavity between sidewalls 44 and the outer periphery of the collar.

Ring 16 is made of an elastic material, such as rubber, and is provided with an axial opening 46 having a diameter smaller than the outer diameter of the shank portion 20 of the puncturing element 12. FIG. 5 illustrates how the ring flexes and remains in frictional contact with the shank 20 when the puncturing element is introduced in the cannula or disassociated therefrom. The ring must remain in sufficient tight constricting engagement with the outer wall of the shank to prevent the exit of $CO_2$. Hence, ring 16 must be able to flex in the longitudinal direction of the displacement of the puncturing instrument or the later-introduced laparoscope instrument; however, its outer edge is restrained from axial displacement by the tight engagement of the collar in the flange recess.

To minimize manufacturing costs. a white high density polyethylene has been used with success for the material of the collar and of the sleeve, however, as mentioned above, other plastics may be used as long as they are stabilized, i.e., stabilizers must be added in the plastic formulation to render them bio-compatible and capable of supporting without discolouration the gamma ray sterilization.

Also, there are other ways of sterilization, however, the gamma ray method has been found to be most efficient. Immersion in a liquid product, uch as the one known under the trademark Cidex, is also possible.

What we claim is:

1. A disposable surgical instrument for use in laparoscopic tubal cauterization and the like for piercing a body cavity, and for thereafter providing communication with said cavity, comprising
   a puncturing instrument made of bio-compatible plastic material, said instrument having substantially constant sections, adapted to be injection moulded, and having a shank portion and a sharp-pointed portion at one end thereof,
   a cannula made of bio-compatible plastic material, said cannula having substantially constant sections, adapted to be injection moulded, and having a hollow elongated portion in surrounding engagement with said shank portion of said instrument and having a flange at one end of said elongated portion,
   a flexible insulating ring secured in said flange and in constricting engagement with said shank portion of said puncturing instrument for providing a seal so that said instrument may be used in laparoscopic tubal cauterization or the like, and
   means for securing said ring in place in said flange by holding peripheral portions thereof in engagement with said flange but allowing middle portions of said ring to flex in the longitudinal axis of said hollow portion as said instrument is introduced into said cannula or disassociated therefrom, said. means comprising tapered interior side wall portions of said flange and a collar in press-fit engagement with said flange interior side wall portions and holding said ring peripheral portions in engagement with said flange.

2. A surgical apparatus as defined in claim 1, further comprising a finger knob mounted at the opposite end of said shank portion of said instrument; said knob abutting against said flange and said collar therein.

3. A surgical apparatus as defined in claim 1, wherein said cannula and said collar are made of a plastic material taken from the group including acetal, polyamide, polyethylene, polyvinylchloride; said plastic material being sterilizable at high temperature.

4. A surgical apparatus as defined in claim 1, wherein said sharp-pointed portion includes spaced cutting edges, diverging from a pointed top, said edges defining smooth surfaces.

5. A surgical apparatus as defined in claim 4, wherein said surfaces define an angle of 15° with the longitudinal axis of said shank portion.

6. A surgical apparatus as defined in claim 5, wherein the end of said cannula opposite the flange includes a tapering portion, said tapering portion defining an angle of 10° with the longitudinal axis of said hollow portion.

7. A surgical apparatus as defined in claim 6, wherein said tapering portion of said cannula is adjacent said surfaces of said sharp-pointed portion to provide easy insertion of the hollow portion of the cannula inside the body cavity.

8. A surgical apparatus as defined in claim 1, wherein the hollow elongated portion of said cannula has a rough outer surface for additional frictional engagement with a cavity wall.

9. A surgical apparatus as defined in claim 1, wherein said flexible ring is made of rubber.

10. A surgical apparatus as defined in claim 2, wherein said puncturing element is made of a transparent polycarbonate so that light, if any, inside the abdominal cavity may be seen through said finger knob via the shank portion.

* * * * *